United States Patent
Jönsson

(10) Patent No.: US 7,959,871 B2
(45) Date of Patent: Jun. 14, 2011

(54) WASH DEVICE FOR DISINFECTION APPARATUS

(75) Inventor: Christer Jönsson, Växjö (SE)

(73) Assignee: Getinge Disinfection AB, Vaxjo (SE)

( * ) Notice: Subject to any disclaimer, the term of this patent is extended or adjusted under 35 U.S.C. 154(b) by 826 days.

(21) Appl. No.: 11/578,703

(22) PCT Filed: Apr. 26, 2005

(86) PCT No.: PCT/SE2005/000605
§ 371 (c)(1),
(2), (4) Date: Jul. 18, 2007

(87) PCT Pub. No.: WO2005/102398
PCT Pub. Date: Nov. 3, 2005

(65) Prior Publication Data
US 2007/0280853 A1    Dec. 6, 2007

(30) Foreign Application Priority Data
Apr. 27, 2004   (SE) ..................... 0401076

(51) Int. Cl.
*A61L 2/18* (2006.01)
(52) U.S. Cl. .................. 422/292; 68/171; 68/172
(58) Field of Classification Search ........... 422/292; 68/3 R, 171, 172, 173
See application file for complete search history.

(56) References Cited

U.S. PATENT DOCUMENTS

| | | | |
|---|---|---|---|
| 3,672,188 A * | 6/1972 | Geschka et al. | 68/12.15 |
| 4,552,728 A | 11/1985 | Taylor | |
| 5,225,160 A | 7/1993 | Sanford et al. | |
| 5,927,616 A * | 7/1999 | Grise et al. | 239/600 |
| 6,041,794 A | 3/2000 | Lin et al. | |
| 6,334,312 B1 | 1/2002 | Mack et al. | |
| 6,354,312 B1 | 3/2002 | Lin et al. | |
| 6,555,054 B1 | 4/2003 | Kral et al. | |
| 6,558,620 B1 | 5/2003 | Sanford et al. | |
| 6,704,946 B1 * | 3/2004 | Mueller et al. | 4/420.4 |
| 2003/0190256 A1 | 10/2003 | Halstead et al. | |

FOREIGN PATENT DOCUMENTS
| FR | 2773325 | 7/1999 |
|---|---|---|
| JP | 11-319039 | 11/1999 |
| JP | 2000-051329 | 2/2000 |

OTHER PUBLICATIONS

Office Action for corresponding European Application No. 05 734 882.3 dated Oct. 2, 2007.

* cited by examiner

*Primary Examiner* — Sean E Conley
(74) *Attorney, Agent, or Firm* — Harness, Dickey & Pierce, P.L.C.

(57) ABSTRACT

A disinfection apparatus for disinfection of objects, such as health care objects, is disclosed. The disinfection apparatus includes a disinfection chamber, and a channel system with at least one wash channel. The wash channel is arranged to transport a cleaning liquid to nozzles directed substantially transversely thereto to distribute cleaning liquid in the disinfection chamber. The wash channel, which supports the nozzles, has a releasable quick coupling which at least at one end engagingly cooperates with the rest of the channel system.

8 Claims, 5 Drawing Sheets

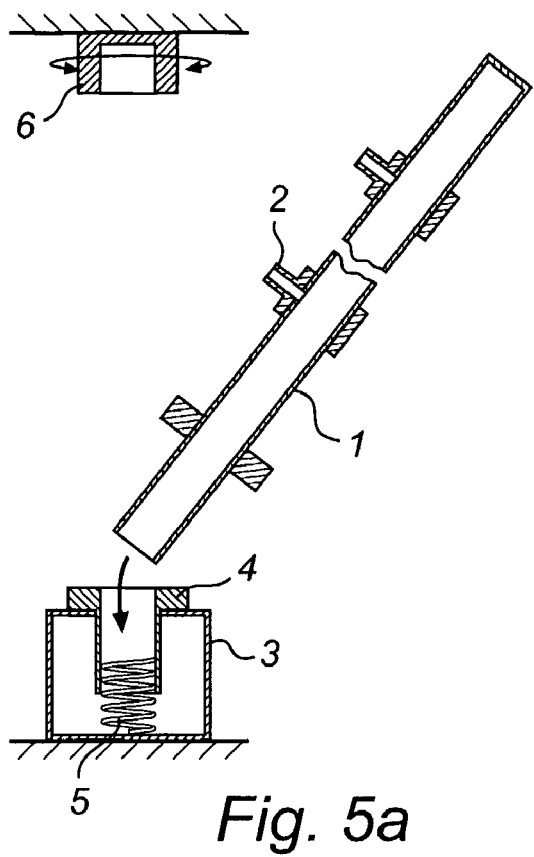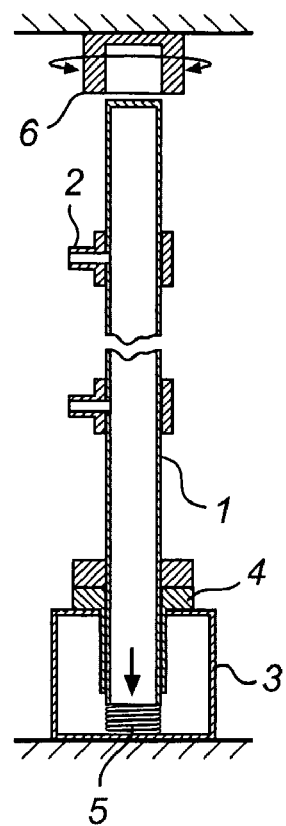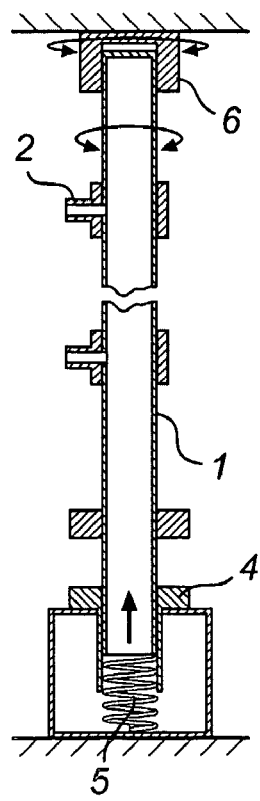
Fig. 5a
Fig. 5b
Fig. 5c

WASH DEVICE FOR DISINFECTION APPARATUS

FIELD OF THE INVENTION

The present invention relates to a disinfection apparatus for disinfection of objects, such as health care objects, which disinfection apparatus comprises a disinfection chamber, a channel system with at least one wash channel. The wash channel is arranged to transport a cleaning liquid to nozzles which are directed substantially transversely thereto to distribute cleaning liquid in said disinfection chamber.

BACKGROUND ART

In medical care, laboratories and in the pharmaceutical industry, disinfection is an important activity to prevent the spread of infection and bacterial growth. There are today a large number of different disinfection apparatus, which are adapted to be installed, for instance, in hospital wards for disinfection of health care objects, surgery equipment, vessels, instrument containers, hospital beds, trolleys, wheelchairs, animal cages, machine parts in nursing applications and other bulky objects.

One type of disinfection apparatus is provided with what is referred to as a walk-in chamber, which is large enough for an individual to enter and/or large enough for a trolley/cart or other equipment to be inserted. As a rule, such a disinfection apparatus comprises a disinfection chamber, into which nozzles open for supplying disinfection fluid. The nozzles are usually connected via a pump to a separate water tank which is supplied from a public water system. It is common for said nozzles of existing disinfection chambers to be arranged on propeller-like arms which are rotated in operation. Such propeller-like arms can be an obstacle to the operator, especially when the arms are mounted at the bottom of the disinfection chamber. In other alternative designs of disinfection apparatus, disinfection nozzles are arranged on what is referred to as a ramp which performs a horizontal or vertical linear motion to distribute disinfecting fluid in the disinfection chamber.

There are, however, a number of drawbacks of prior-art technique as described above, for instance the rotary or linear motion can be prevented by objects that are to be disinfected and by mistake obstruct the moving device. Moreover, nozzles and movable arms/beams can be difficult to dismount when replacing components, in cleaning, in maintenance or in repair works. Other problems of prior-art technique may involve the performance of effective cleaning of the objects in the disinfection chamber, since the objects are only cleaned for a short period of time in the same place. This requires time-consuming cleaning programmes for a satisfactory disinfection result.

To enable quick and acceptable disinfection, it is desirable to provide an adequate spray pattern in the disinfection chamber. It is further desirable to be able to reduce the number of machine components of the disinfection apparatus while maintaining its desired disinfecting function.

Finally it is advantageous to provide a robust, cost-effective and reliable high Quality disinfection apparatus.

SUMMARY OF THE INVENTION

The object of the present invention is to provide a disinfection apparatus which enables improvements in relation to prior-art disinfection apparatus in one or more of the above-mentioned aspects.

The object is achieved by a disinfection apparatus of the type mentioned by way of introduction, which is further characterised in that the wash channel which supports said nozzles has a releasable quick coupling which at least at one end engagingly cooperates with the rest of the channel system.

The present invention as defined in claim 1 gives several advantages, such as more effective cleaning and disinfection and improved intensity in the spray pattern of the nozzles in relation to prior art.

In this case, the term quick coupling refers to a connection using simple manipulations or tools which is not time-consuming but effectively can facilitate mounting/dismounting.

In the disinfection apparatus, the wash channel preferably is a releasable complementary part to the rest of the channel system. Moreover, said wash channel is axially movable for releasable connection to the rest of the channel system. This ensures safe and reliable connection between the wash channel and the rest of the channel system feeding fluid to the wash pipe. This type of form fitting ensures safe holding of the wash pipe, which thus cannot, for instance, easily come loose in operation.

Preferably, at least one end of said wash channel is arranged for axially spring-loaded insertion into a first receiving sleeve of the rest of the channel system for releasable connection. Such spring-loaded insertion allows the spring force to be used to hold the wash channel in a desired mounting position. A spring-loaded quick coupling can by simple means be designed for operation without tools, which allows simple and effective handling.

A second receiving sleeve is preferably arranged at the other end of the wash channel. In this way, the wash channel can be arranged to be inserted into the first receiving sleeve which has a greater insertion distance than the possible insertion distance of the second receiving sleeve. This allows releasable connection of the wash channel to said channel system. This arrangement can be considered to constitute a quick coupling. The wash channel is advantageously spring-loaded against the second receiving sleeve and, owing to the difference in insertion distance, the wash channel is pressed against the second receiving sleeve in the mounted position.

Said wash channel is preferably rotatably arranged on its longitudinal axis for distributing cleaning liquid in the disinfection chamber. The wash channel can be arranged horizontally or vertically or in any other direction to obtain an effective wash pattern and, thus, adequate disinfection.

The rotatably arranged wash channel advantageously performs in use an oscillating rotary motion in order to distribute washing liquid in the disinfection chamber. In this way, accurate cleaning of the objects in the chamber is provided.

Preferably, at least one of said first and second receiving sleeves is arranged with a spring means for receiving said wash channel. This spring means may consist of, for instance, a coil spring which presses the wash channel in position. Moreover, a spring allows liquid to flow through the same and in this way the transfer of liquid from the rest of the channel system to the wash channel occurs in a simple manner.

A set of wash channels are preferably connectable to the rest of the channel system, said wash channels being individually replaceable. This is advantageous, for example, by repair work being simplified, and moreover wash pipes can be adjusted individually to different positions, and in this way disinfection is optimised.

Preferably, said rest of the channel system for supply of liquid is arranged with a plurality of said first receiving sleeves, which are arranged spaced from each other and adjusted to a plurality of the respective wash channels. By using a plurality of oscillatingly rotating wash pipes, for instance letting the pipe rotate for parts of a turn back and forth, a good disinfection and rinsing result can be achieved.

Wash channels are preferably arranged substantially vertically along the side walls of the disinfection chamber. In this way intensive cleaning of the objects in the chamber is provided, which can be used, for instance, by saving time for the entire disinfection programme.

Different types of wash pipes can be used, for instance with regard to their location in the chamber. A wash pipe placed in a corner, along a side or in the centre of the chamber can be designed in various ways and with different types of nozzles. Moreover it is possible to use different types of wash or spray nozzles in different positions along a wash pipe so as to provide an effective spray pattern with regard to the objects in the chamber that are to be disinfected.

BRIEF DESCRIPTION OF DRAWINGS

The invention will now be described with reference to the accompanying drawings, which for the purpose of exemplification illustrate preferred embodiments of the invention.

FIG. 5a is a sectional view of a wash pipe in a first mounting position.

FIG. 5b is a sectional view of a wash pipe in a second mounting position.

FIG. 5c is a sectional view of a wash pipe in a mounted position.

DESCRIPTION OF PREFERRED EMBODIMENTS

Figure 1:
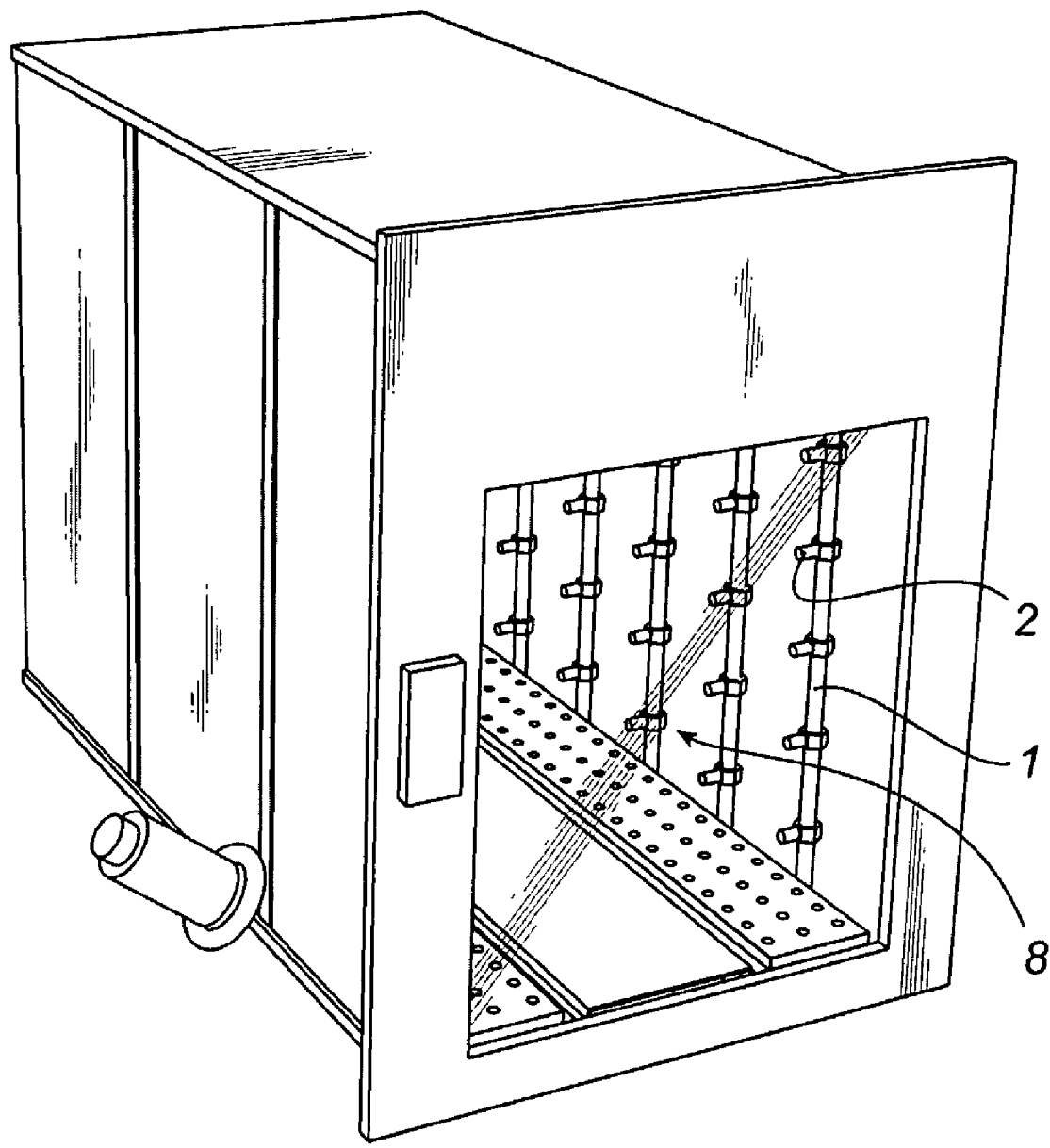
FIG. 1 is a perspective schematic view of a disinfection apparatus according to the invention.

FIG. 1 shows a disinfection apparatus with a chamber 8, which is adapted to receive objects for disinfection. The chamber 8 is partly made from mountable wall, ceiling and floor elements of, for instance, stainless sheet steel. Moreover a movably arranged door is mounted for opening and closing the entrance of the chamber.

Figure 2:
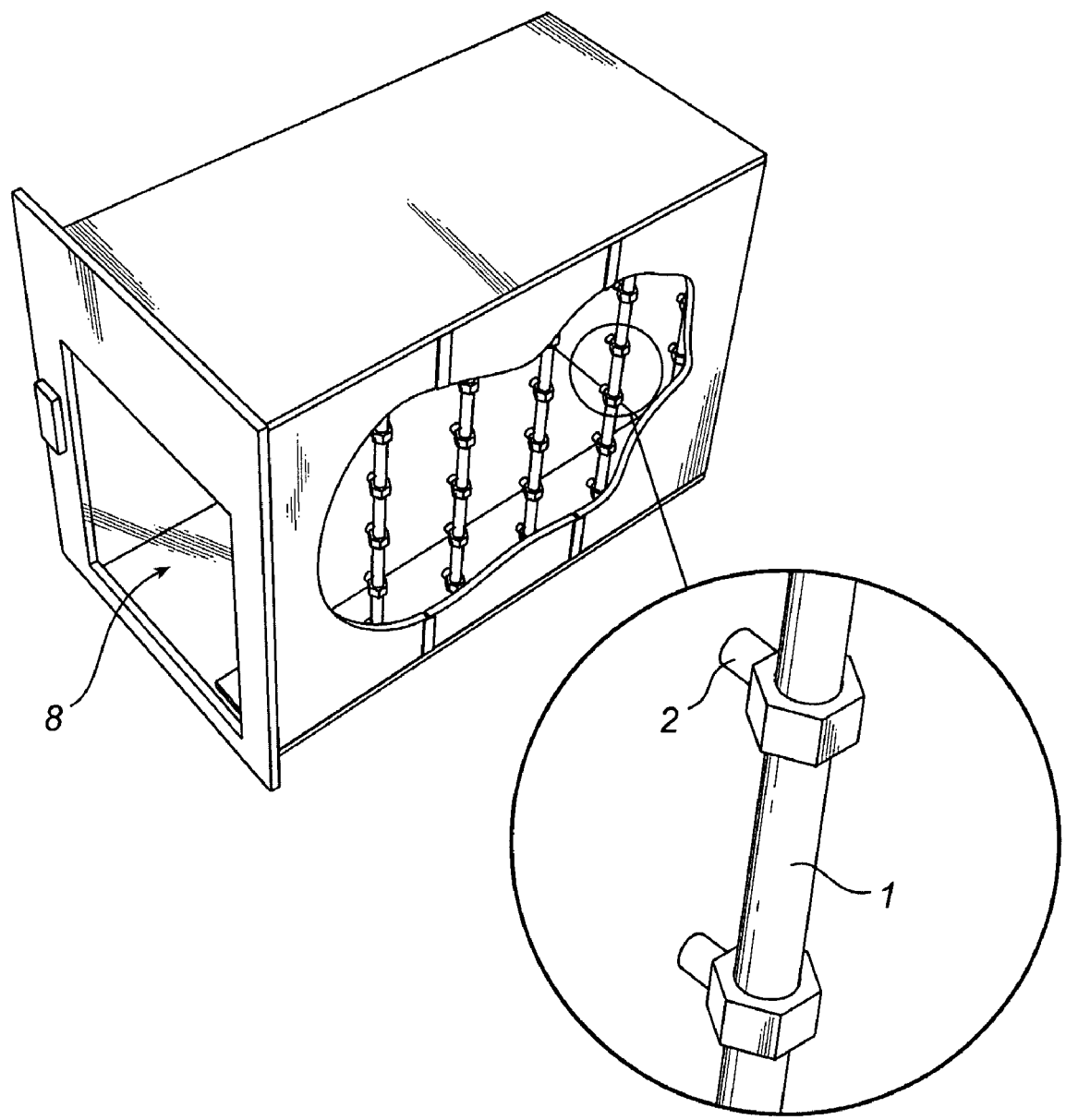
FIG. 2 is a perspective view, seen obliquely from the front, of parts of the disinfection apparatus in FIG. 1 in more detail, partly in section and a part of a wash pipe with nozzles being enlarged.

FIG. 2 shows a disinfection apparatus similar to the one in FIG. 1. Spray nozzles 2, here also referred to as wash nozzles, are equidistantly spaced from each other on the vertical wash pipes 1. The wash nozzles 2 can be positioned at different levels and directed at different angles to provide an effective spray pattern in the chamber 8. In the embodiment shown, wash pipes are positioned along the two side walls in relation to the door. However, it is conceivable to position wash pipes in other ways in other embodiments, such as in the ceiling, on the rear wall or in the centre of the chamber.

Figure 3:
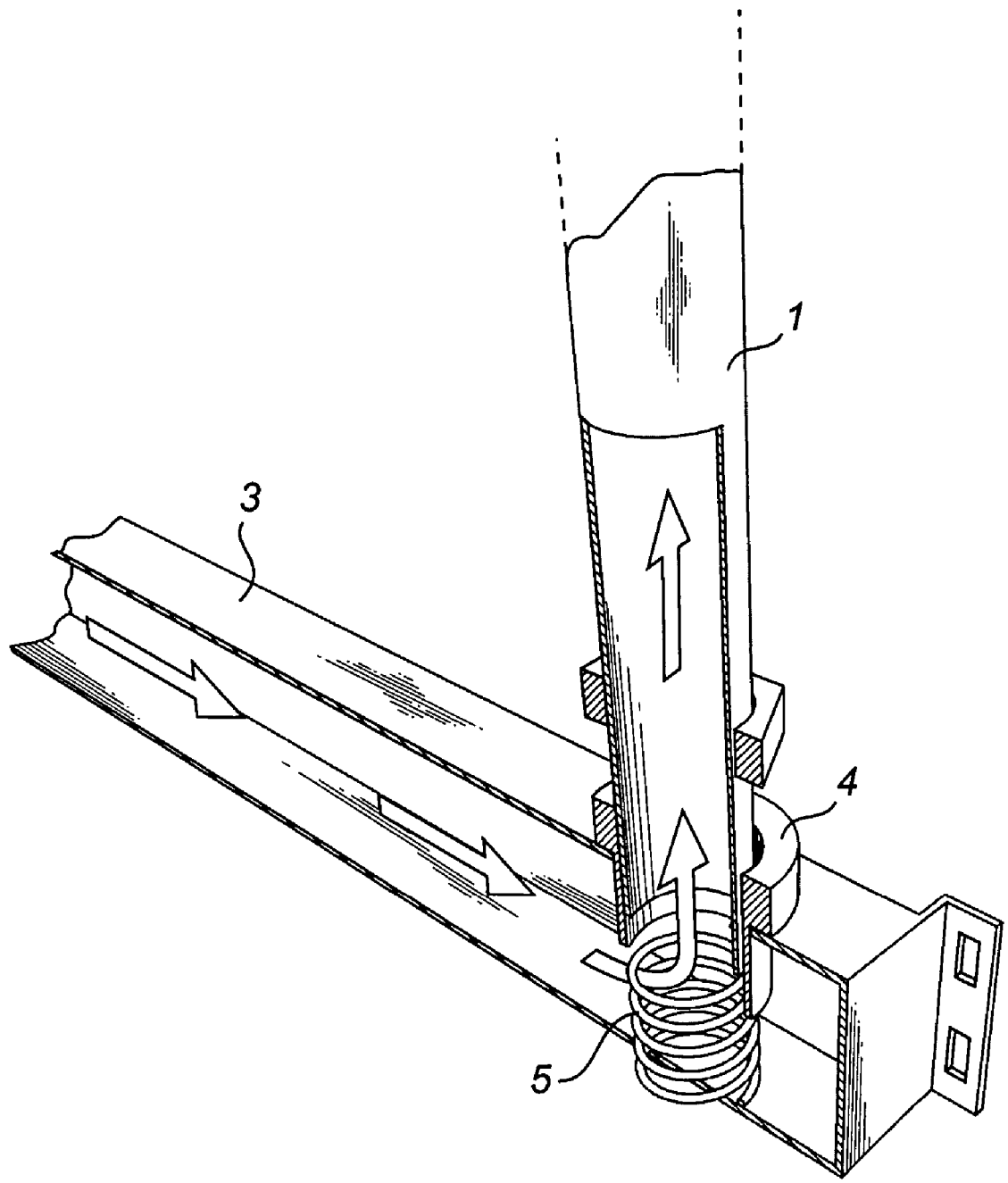
FIG. 3 is a sectional view in perspective of the path of the disinfection liquid up to and through a wash pipe.

A detailed section through the lower attachment of the wash pipe is shown in FIG. 3, from which it is evident how the cleaning liquid flows through the channel 3 up to the opening of the wash pipe where the spring 5 allows liquid to flow into the wash pipe 1 for further transport to the wash nozzles 2. The channel 3 is in this embodiment a square section which can be attached to an adjoining surface, for instance a side wall inside the chamber 8. The spring 5 presses the wash pipe 1 upwards in the mounted position and thus forms a gap adjacent to the spring 5 which allows liquid to flow through the spring 5. The receiving sleeve 4 which is mounted in the channel 3 keeps the spring 5 in place and serves as a guide and seal for the pipe 1.

In this embodiment, the spring 5 of the quick coupling is arranged in the lower attachment of the wash pipe 1, but it is conceivable according to an alternative embodiment for the spring to be arranged in the upper attachment of the pipe 1.

Figure 4:
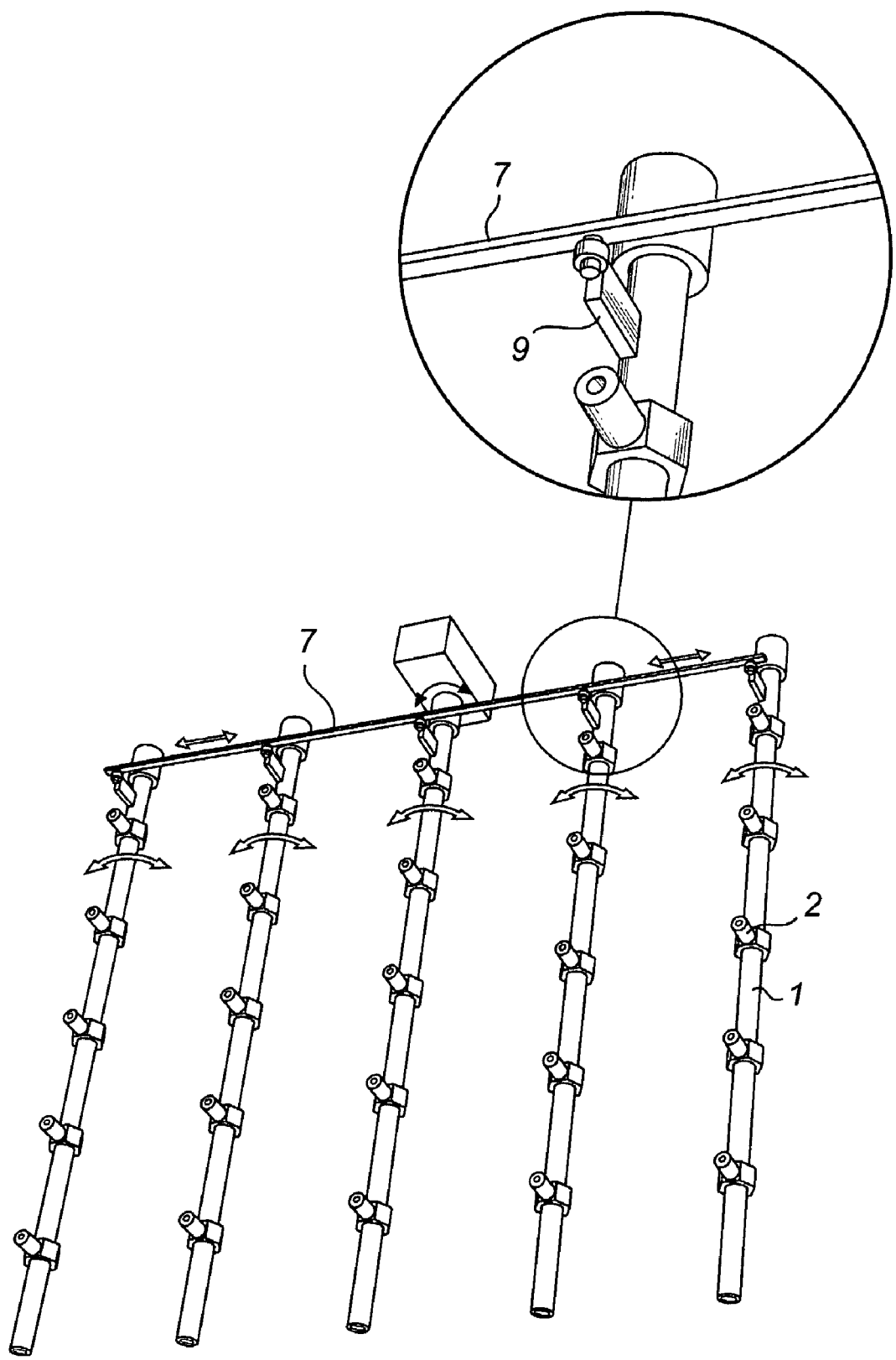
FIG. 4 is a perspective view of the motion of a set of wash pipes in operation.

It is evident from FIG. 4 how a set of wash pipes 1 are driven to an oscillating rotary motion. In this embodiment, the wash pipes 1 are rotated at an angle which preferably is between 40° and 160°, more preferred between 90° and 130° and most advantageously 120° about their respective longitudinal axes. This rotation is repeated back and forth to spray liquid on the objects which are to be disinfected in the chamber 8. This occurs, for instance, in the washing, cleaning and other phases of the disinfection programme.

It is also evident from FIG. 4 how the drive of the wash pipes 1 occurs. A motor or some other device is connected to one of the wash pipes to perform the rotary motion. To transfer the motion to the other wash pipes, arms 9 are arranged on the respective wash pipes 1 which in turn are connected to a strut 7 which transfers the motion to the set of wash pipes. In this embodiment, a transferring strut (not shown) is arranged, for instance, to transfer a motion from one side wall for a set of pipes to another set of pipes. The above design for providing the oscillating rotary motion of the pipes 1 requires only one sealed lead-in, from a motor for instance, to the chamber. A person skilled in the art can vary how the drive of the motion of the wash pipes occurs.

FIG. 5 shows the mounting process for a wash pipe 1 according to a first embodiment of the invention. According to FIG. 5a, the wash pipe 1 is first angled so that it goes clear of the second upper receiving sleeve 6 or the holder. Then the first lower end of the wash pipe is inserted into the first receiving sleeve 4. When the first lower end of the wash pipe is inserted into the first receiving sleeve 4, the end of the pipe compresses a spring 5 in the sleeve, after which the wash pipe 1 can be angled to a position that allows its second end to be inserted into the second receiving sleeve 6. This motion is promoted by a spring 5 of the first sleeve 4 which wants to press the wash pipe 1 towards the second receiving sleeve 6. Since the insertion distance of the first receiving sleeve 4 is greater than the insertion distance of the second receiving sleeve 4, the wash pipe 1 is kept in place by the coil spring 5. The dismounting process for a wash pipe 1 is the same as the mounting process but in reverse order.

FIG. 5 shows that the wash channel is closed at its upper end. Besides the upper sleeve 6 is rotatably arranged and thus turned with the wash pipe 1 in operation in order to distribute liquid. In an alternative embodiment, the wash pipe 1 is arranged with the open end turned upwards, and in this case the upper and lower attachments change places, so that the supply of liquid occurs from above.

It will be appreciated that the above-described embodiments of the invention can be modified and varied by a person skilled in the art without departing from the inventive concept defined in the claims. For instance, liquid can be supplied from both ends of the wash pipe 1. For example, the first lower receiving sleeve 4 can be designed so that liquid passes through its side wall, for instance by the sleeve extending down to the bottom of the channel 3 and the sleeve being formed with recesses in the side wall to allow fluid to flow into the pipe 1. In view of that illustrated in FIGS. 1-5, it should not be considered to be excluded to arrange wash nozzles also in other positions in the chamber 8; for instance stationary or moving nozzles can be placed directly on the rest of the channel system. Moreover the wash pipes 1 can be adjusted for use in connection with the drying for supplying, for instance, hot air to the chamber 8.

Different types of wash nozzles can be used and they can also be directed in different ways, for instance depending on their location along the wash pipe. For instance, wash nozzles which are arranged far down on a wash pipe can be directed upwards at an angle.

The wash pipe 1 need not necessarily have a straight elongate extent but can alternatively be, for instance, curved, shaped or arranged with projecting portions to achieve the desired effects in the distribution of fluid in the disinfection chamber 8.

Moreover, for instance, wash pipes or sets of wash pipes can be arranged so as to extend transversely through the disinfection chamber in order to optimise cleaning.

The invention claimed is:

1. A disinfection apparatus for disinfection of objects, the disinfection apparatus comprising:
   a disinfection chamber; and
   a channel system for distributing cleaning liquid in said disinfection chamber,
   said channel system including:
   at least one wash pipe comprising nozzles directed substantially transversely to said wash pipe to distribute said cleaning liquid in the disinfection chamber; and
   a channel for providing said cleaning liquid to the wash pipe,
   said channel comprising a first receiving sleeve where a first end of said wash pipe is inserted, and
   said disinfection apparatus further comprising a second receiving sleeve where a second end of said wash pipe is inserted,
   wherein said first end is axially spring loaded by a spring arranged at said first receiving sleeve, and
   wherein a maximum insertion distance of said wash pipe into said first receiving sleeve is greater than a maximum insertion distance of said wash pipe into said second receiving sleeve to allow releasable connection of the wash pipe to said channel.

2. A disinfection apparatus as claimed in claim 1, wherein said wash pipe is rotatably arranged on its longitudinal axis for distribution of said cleaning liquid.

3. A disinfection apparatus as claimed in claim 2, wherein the rotatably arranged wash pipe in use performs an oscillating rotary motion in order to distribute said cleaning liquid.

4. A disinfection apparatus as claimed in claim 1, wherein a set of wash pipes are connected to said channel, said wash pipes being individually replaceable.

5. A disinfection apparatus as claimed in claim 1, wherein said channel comprises a plurality of first receiving sleeves, which are arranged spaced from each other and adjusted to a plurality of the respective wash channels.

6. A disinfection apparatus as claimed in claim 1, wherein said wash pipes are arranged substantially vertically along side walls of the disinfection chamber.

7. A disinfection apparatus as claimed in claim 1, wherein the spring is disposed to allow the cleaning liquid to pass therethrough.

8. A disinfection apparatus as claimed in claim 1, wherein the spring is disposed in both the channel and the first receiving sleeve.

* * * * *

UNITED STATES PATENT AND TRADEMARK OFFICE
CERTIFICATE OF CORRECTION

PATENT NO. : 7,959,871 B2  
APPLICATION NO. : 11/578703  
DATED : June 14, 2011  
INVENTOR(S) : Christer Jönsson Page 1 of 1

It is certified that error appears in the above-identified patent and that said Letters Patent is hereby corrected as shown below:

On the title page, item 30, Foreign Application Priority Data, reads:

Apr. 27, 2004    (SE)    0401076 item 30, Foreign Application Priority Data, should read:

Apr. 27, 2004    (SE)    0401076-5

Signed and Sealed this  
Thirteenth Day of September, 2011

David J. Kappos  
*Director of the United States Patent and Trademark Office*